United States Patent
Naqvi et al.

(10) Patent No.: US 12,220,225 B2
(45) Date of Patent: *Feb. 11, 2025

(54) SYSTEMS, METHODS, AND APPARATUSES FOR PERIPHERAL ARTERIAL DISEASE DETECTION AND MITIGATION THEREOF

(71) Applicant: NEW LIFEWARE INC., Bloomingdale, IL (US)

(72) Inventors: Syed R. Naqvi, Bloomingdale, IL (US); Abbas S. Ali, Orlando, FL (US)

(73) Assignee: New Lifeware Inc., Bloomingdale, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/295,116

(22) Filed: Apr. 3, 2023

(65) Prior Publication Data
US 2023/0248262 A1 Aug. 10, 2023

Related U.S. Application Data

(60) Continuation of application No. 16/802,699, filed on Feb. 27, 2020, now Pat. No. 11,642,044, which is a
(Continued)

(51) Int. Cl.
*A61B 5/00* (2006.01)
*A61B 5/02* (2006.01)
(Continued)

(52) U.S. Cl.
CPC ........ *A61B 5/1072* (2013.01); *A61B 5/02007* (2013.01); *A61B 5/1073* (2013.01);
(Continued)

(58) Field of Classification Search
CPC . A61B 5/1072; A61B 5/02007; A61B 5/1073; A61B 5/1075; A61B 5/4833;
(Continued)

(56) References Cited

U.S. PATENT DOCUMENTS 5,065,414 A    11/1991  Endou et al.
5,732,475 A *   3/1998  Sacks .................. A61B 5/1073
                                                    33/555.4
(Continued)

OTHER PUBLICATIONS

"Chronic Changes in Skeletal Muscle Histology and Function in Peripheral Arterial Disease" by Regensteiner, May 7, 2020.*
(Continued)

*Primary Examiner* — Omar Casillashernandez
(74) *Attorney, Agent, or Firm* — WEAVER IP L.L.C.

(57) ABSTRACT

Embodiments described herein are directed to non-invasive detection of peripheral arterial disease. For example, a measuring apparatus is used to measure a patient's calf circumference. The measuring apparatus has text feature(s) or indicator(s) printed thereupon that indicate the likelihood that the patient has peripheral arterial disease based on the measured calf circumference. The assessment may be further refined by using a software application that assesses the likelihood of the patient having peripheral arterial disease using at least the calf circumference measurement, along with other information/data. Based on the assessment, a healthcare practitioner may prescribe a walking program for the patient to follow. A software application may track compliance of the walking program and provide escalating reminders to the patient if the patient continues to fail to comply with the prescribed walking program.

8 Claims, 7 Drawing Sheets

Related U.S. Application Data division of application No. 15/443,944, filed on Feb. 27, 2017, now Pat. No. 10,716,493.

(51) Int. Cl.

| | | |
|---|---|---|
| *A61B 5/107* | (2006.01) | |
| *G01B 3/1003* | (2020.01) | |
| *G01B 3/1084* | (2020.01) | |
| *G16H 20/30* | (2018.01) | |
| *G16H 50/20* | (2018.01) | |
| *G16H 50/30* | (2018.01) | |
| *G01C 22/00* | (2006.01) | |

(52) U.S. Cl.
CPC .......... *A61B 5/1075* (2013.01); *G01B 3/1003* (2020.01); *G01B 3/1084* (2013.01); *G16H 20/30* (2018.01); *G16H 50/20* (2018.01); *G16H 50/30* (2018.01); *A61B 5/4833* (2013.01); *G01C 22/006* (2013.01)

(58) Field of Classification Search
CPC .... G01B 3/1003; G01B 3/1084; G16H 20/30; G16H 50/20; G16H 50/30; G01C 22/006
USPC .......................................................... 600/587
See application file for complete search history.

(56) References Cited

U.S. PATENT DOCUMENTS

| | | |
|---|---|---|
| 8,462,591 B1 | 6/2013 | Marhaben |
| 10,716,493 B2 | 7/2020 | Naqvi et al. |
| 11,642,044 B2 | 5/2023 | Naqvi et al. |
| 2001/0051327 A1 | 12/2001 | Hatano et al. |
| 2003/0005766 A1 | 1/2003 | Guzman |
| 2004/0140348 A1 | 7/2004 | Fromm |
| 2006/0155494 A1 | 7/2006 | Kato et al. |
| 2008/0154099 A1 | 6/2008 | Aspel et al. |
| 2013/0187780 A1 | 7/2013 | Angelides |
| 2014/0039839 A1 | 2/2014 | Yuen et al. |
| 2014/0297395 A1 | 10/2014 | Chao et al. |
| 2015/0205930 A1 | 7/2015 | Shaanan et al. |
| 2015/0269827 A1 | 9/2015 | Hopkins et al. |
| 2016/0203691 A1 | 7/2016 | Arnold et al. |
| 2016/0271451 A1 | 9/2016 | Wu et al. |
| 2016/0283044 A1 | 9/2016 | Ohsawa |
| 2016/0284172 A1 | 9/2016 | Weast et al. |
| 2016/0324444 A1* | 11/2016 | Abdel-Rahman .... A61B 5/1075 |
| 2017/0249280 A1 | 8/2017 | Wu et al. |
| 2018/0121828 A1 | 5/2018 | Keysers et al. |
| 2018/0242885 A1 | 8/2018 | Naqvi et al. |
| 2020/0196909 A1 | 6/2020 | Naqvi et al. |

OTHER PUBLICATIONS

U.S. Appl. No. 15/443,944, filed Feb. 27, 2017, Naqvi et al.
U.S. Appl. No. 16/802,699, filed Feb. 27, 2020, Naqvi et al.
Hoechstmass, Amazon, "Hoechstmass Multi-color Soft Measuring Tapes" First Available Jun. 8, 2015. Retrieved from <https://www.amazon.com/Hoechstmass-Multi-color-Measuring-Sewing-Germany/dp/B00Z70WWJ0> on Aug. 5, 2019. (Year: 2015).
Ali et al., "Quantification of Soft Tissue Loss Among Patients with Peripheral Arterial Disease", The Journal for Vascular Ultrasound, vol. 40, No. 1, Mar. 2016, pp. 20-23.
Regensteiner et al., "Chronic Changes in Skeletal Muscle Histology and Function in Peripheral Arterial Disease", Circulation, vol. 87, No. 2, Feb. 1993, pp. 413-421.

* cited by examiner

SYSTEMS, METHODS, AND APPARATUSES FOR PERIPHERAL ARTERIAL DISEASE DETECTION AND MITIGATION THEREOF

CROSS-REFERENCE TO RELATED APPLICATIONS

The present application is continuation of U.S. application Ser. No. 16/802,699, entitled "SYSTEMS, METHODS, AND APPARATUSES FOR PERIPHERAL ARTERIAL DISEASE DETECTION AND MITIGATION THEREOF," filed on Feb. 27, 2020, now allowed, which is a divisional application of U.S. application Ser. No. 15/443,944, entitled "SYSTEMS, METHODS, AND APPARATUSES FOR PERIPHERAL ARTERIAL DISEASE DETECTION AND MITIGATION THEREOF," filed on Feb. 27, 2017, now U.S. Pat. No. 10,716,493, both of which are incorporated by reference herein.

BACKGROUND

Technical Field

The present application relates to methods, systems, and apparatuses for non-invasive procedures for detecting and mitigating peripheral arterial disease.

Background Art

Peripheral arterial disease is a common circulatory problem in which narrowed arteries reduce blood flow to a person's limbs. When peripheral arterial disease is developed, the extremities (e.g., a person's legs) do not receive enough blood flow to keep up with the demand. This causes various symptoms, most notably leg pain when walking. Severe peripheral arterial disease can lead to even more extreme issues, such as kidney failure, foot or leg amputation, a heart attack, or a stroke. Certain procedures, such as an angiogram or a blood test, can be used to detect the presence of peripheral arterial disease. However, such procedures are invasive and generally disliked by patients.

BRIEF SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Methods, systems, and apparatuses are described for non-invasive procedures for detecting and mitigating peripheral arterial disease, substantially as shown in and/or described herein in connection with at least one of the figures, as set forth more completely in the claims.

Further features and advantages of the invention, as well as the structure and operation of various embodiments, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form a part of the specification, illustrate embodiments and, together with the description, further serve to explain the principles of the embodiments and to enable a person skilled in the pertinent art to make and use the embodiments.

Figure 1A:
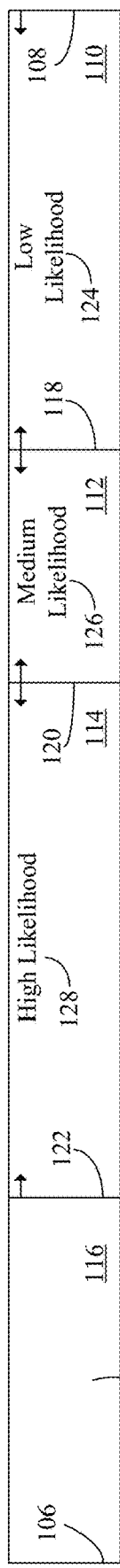
FIG. 1A shows a block diagram of a first surface of a measuring apparatus for determining a calf circumference of a patient for diagnosing peripheral arterial disease in accordance with an embodiment.

The features and advantages of the embodiments described herein will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

I. Introduction

The present specification discloses numerous example embodiments. The scope of the present patent application is not limited to the disclosed embodiments, but also encompasses combinations of the disclosed embodiments, as well as modifications to the disclosed embodiments.

References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Furthermore, it should be understood that spatial descriptions (e.g., "above," "below," "up," "left," "right," "down," "top," "bottom," "vertical," "horizontal," "front," "rear," etc.) used herein are for purposes of illustration only, and that practical implementations of the structures described herein can be spatially arranged in any orientation or manner.

Numerous exemplary embodiments are described as follows. It is noted that the section/subsection headings used herein are not intended to be limiting. Embodiments described in this document may be eligible for inclusion within multiple different sections or subsections. Furthermore, disclosed embodiments may be combined with each other in any manner.

Embodiments described herein are directed to non-invasive detection of peripheral arterial disease. For example, a measuring apparatus may be used to measure the calf circumference a patient. The measuring apparatus may have one or more text features or indicators printed thereupon that indicate the likelihood that the patient has peripheral arterial disease based on the measured calf circumference. The assessment may be further refined by using an application that assesses the likelihood of the patient having peripheral arterial disease using at least the calf circumference measurement, along with other information/data, such as a toe brachial index measurement associated with the patient, results of a walking test performed by the patient, and/or symptom-related information obtained from a questionnaire filled out by the patient. Based on the assessment, a healthcare practitioner (e.g., a doctor, a nurse, a physician's assistant, etc.) may prescribe a walking program for the patient to follow. An application may track compliance of the walking program and provide escalating reminders to the patient if the patient continues to fail to comply with the prescribed walking program.

In particular, a measuring apparatus for determining a calf circumference of a patient for diagnosing peripheral arterial disease is described herein. The measuring apparatus comprises a strip of material. The strip of material comprises a first surface and a second surface that opposes the first surface. At least one of the first surface or the second surface comprises a plurality of color-coded segments arranged in series. A first segment of the plurality of color-coded segments has a first color and corresponds to a first range of calf circumference that represents a high likelihood that the patient has peripheral arterial disease. A second segment of the plurality of color-coded segments has a second color that is different than the first color and corresponds to a second range of calf circumference that represents a low likelihood that the patient has peripheral arterial disease.

A method performed by a computer associated with a healthcare practitioner to determine compliance of a walking program prescribed by the healthcare practitioner is also described herein. In accordance with the method, first sensor data is received from a mobile device via a network that indicates a first number of steps a patient has taken within a predetermined time period. A determination is made that the first number of steps the patient has taken within the predetermined time period is not in compliance with the walking program prescribed by the healthcare practitioner. A first message having a first severity is transmitted via the network to a device associated with the patient indicating that the patient did not comply with the prescribed walking program.

A system is also described herein. The system includes at least one processor circuit and at least one memory that stores program code configured to be executed by the at least one process circuit. The program code includes a receiver configured to receive, via a network, first sensor data from a mobile device that indicates a first number of steps a patient has taken within a predetermined time period. The program code also includes a compliance determiner configured to determine that the first number of steps the patient has taken within the predetermined time period is not in compliance with a walking program prescribed by a healthcare practitioner. The program code further includes a transmitter configured to transmit, via the network, a first message having a first severity to a device associated with the patient indicating that the patient did not comply with the prescribed walking program.

These and further embodiments and variations are described in the next section.

II. Example Embodiments

A. Measuring Apparatus Evaluation Assessment

Figure 1B:
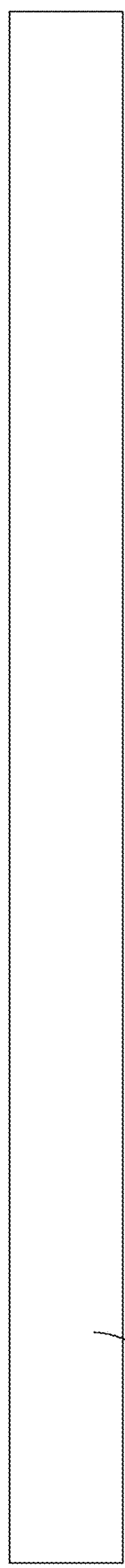
FIG. 1B shows a block diagram of a second surface that opposes the first surface of the measuring apparatus depicted in FIG. 1A in accordance with an embodiment.

FIGS. 1A and 1B are block diagrams of a measuring apparatus 100 for determining a calf circumference of a patient for diagnosing peripheral arterial disease in accordance with an embodiment. As shown in FIGS. 1A and 1B, measuring apparatus 100 comprises a first surface 102 and a second surface 104 that opposes first surface 102. First surface 102 may also be referred to as a front or outer surface of measuring apparatus 100, and second surface 104 may also be referred to as a back or inner surface of measuring apparatus 100. Measuring apparatus 100 may be a strip of material having a starting point 106 (a first edge) and an ending point 108 (a second edge opposed to the first edge). As shown in FIGS. 1A and 1B, the strip may be a substantially rectangular shape, although embodiments described herein are not so limited. The material of which measuring apparatus 100 is made may comprise paper, plastic, cloth, fiber glass, metal, metal alloy, and/or any combination thereof.

First surface 102 may comprise a plurality of segments 110, 112, 114, and 116 that are arranged in series between starting point 106 and ending point 108. Each of segments 110, 112, 114, and 116 may be defined via starting point 106, ending point 108 and one or more segment markers 118, 120, and 122 printed thereupon between them. For example, first segment 110 may be defined by the portion of first surface 102 between ending point 108 and segment marker 118. Second segment 112 may be defined by the portion of first surface 102 between segment marker 118 and segment marker 120. Third segment 114 may be defined by the portion of first surface 102 between segment marker 120 and segment marker 122. Fourth segment 116 may be defined by the portion of first surface 102 between segment marker 122 and starting point 106.

Each segment of measuring apparatus 100 may correspond to a calf thickness and corresponding likelihood that a patient has peripheral arterial disease. For instance, in an embodiment, first segment 110 corresponds to a first range of calf thickness that represents a low likelihood that the patient has peripheral arterial disease. Second segment 112 corresponds to a second range of calf thickness that represents a medium likelihood that the patient has peripheral arterial disease. Third segment 114 corresponds to a third range of calf thickness that represents a high likelihood that the patient has peripheral arterial disease. Fourth segment 116 may be a portion of measuring apparatus 110 that a user holds while wrapping measuring apparatus 100 around the calf of the patient and may not be used as an indicator of the likelihood that the patient has peripheral arterial disease. It is further noted that while measuring apparatus 100 is depicted as having four segments (i.e., segments 110, 112, 114, and 116), measuring apparatus 100, in other embodiments, other numbers of segments may be present that correspond to calf thicknesses and disease likelihoods.

As shown in FIG. 1A, one or more segments may include markings printed thereupon that are indicative of the likelihood that the patient has peripheral arterial disease. For example, first segment 110 may include a text feature 124 ("Low Likelihood"), second segment 112 may include a text feature 126 ("Medium Likelihood"), and third segment 114 may include a text feature 128 ("High Likelihood"). It is noted that text features 124, 126, and 128 are merely exemplary and that any text and/or graphical feature may be used to represent various likelihoods of a patient having peripheral arterial disease. Fourth segment 116 may not include any markings printed thereupon (i.e., segment 116 may be blank) or may indicate fourth segment 116 as intended for a user's hand, etc.

Measuring apparatus 100 and each segment thereof may have a corresponding length. For instance, in accordance with an embodiment, the length of measuring apparatus is approximately 60 cm (e.g., measuring apparatus 100 may have a length between 59 and 61 cm). In accordance with such an embodiment, first segment 110 is approximately 17 centimeters in length (e.g., first segment 110 may have a length between 16-18 centimeters), second segment 112 is approximately 9 centimeters in length (e.g., second segment 112 may have a length between 8-10 centimeters), third segment 114 is 20 centimeters in length (e.g., third segment 110 may have a length between 19-21 centimeters), and fourth segment 116 is approximately 14 centimeters in length (e.g. fourth segment 116 may have a length between 13-15 centimeters).

In an embodiment, the length of each of segments 110, 112, and 114 may be based on statistical analysis of data associated with a plurality of patients (e.g., thousands of patients). The data may be maintained in a public database (e.g., a National Health and Nutrition Examination Survey (NHANES) database) that includes information regarding patients with and without peripheral arterial disease. After applying a generalized linear statistical model and/or a random forest machine learning model to the data, and after controlling for traditional risk factors (e.g., age, ethnicity, smoking, hypertension, body mass index (BMI)), it has been observed that calf circumference is a strong independent predictor of the present of peripheral arterial disease. In particular, it has been observed that a calf circumference less than 34 cm is an indicator that a patient has a high likelihood of having peripheral arterial disease, a calf circumference greater than 43 cm is an indicator that a patient has a low likelihood of having peripheral arterial disease, and a calf circumference having a range therebetween (e.g., between 34 cm and 43 cm) is an indicator that a patient has a medium likelihood of having peripheral arterial disease.

As also shown in FIG. 1B, second surface 104 may be blank (i.e., second surface 104 may have not markings printed thereupon). Alternatively, second surface 104 may have the same markings as first surface 102. That is, second surface 104 may be identical to first surface 102.

Figure 2:
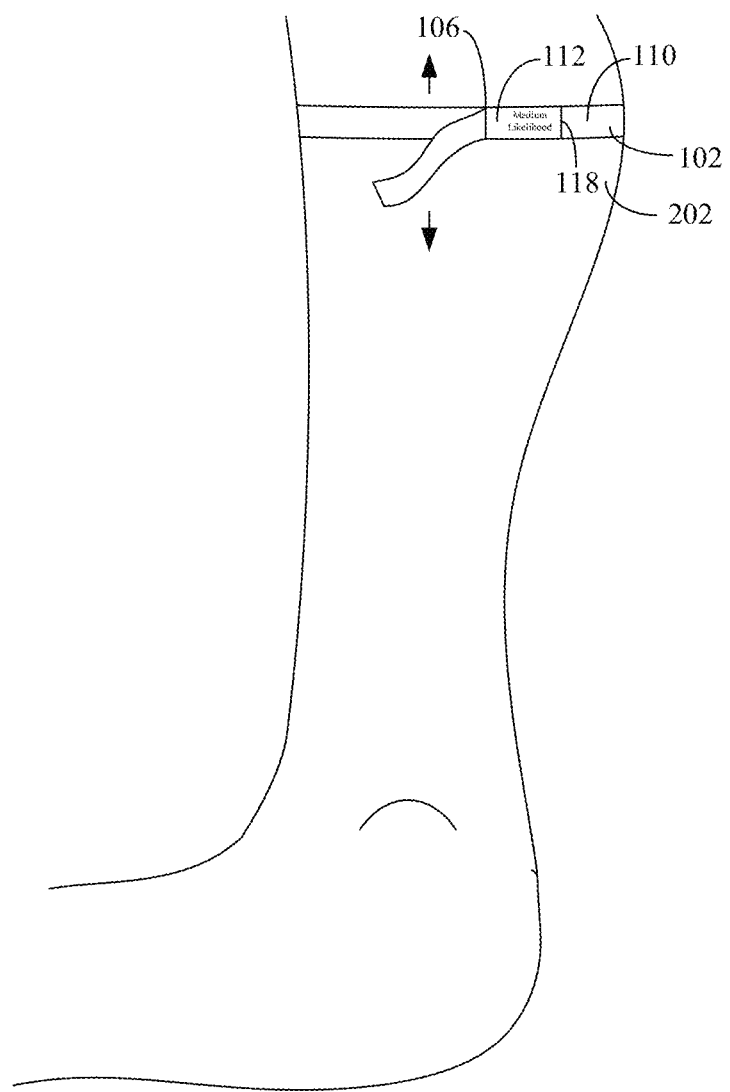
FIG. 2 shows a diagram illustrating the measuring of the circumference of a patient's calf using a measuring apparatus in accordance with an embodiment.

The likelihood that the patient has peripheral arterial disease may be determined by measuring the circumference of the calf of the patient using measuring apparatus 100. For example, FIG. 2 shows a diagram 200 illustrating the measuring the circumference of a patient's calf using measuring apparatus 100 in accordance with an embodiment. As shown in FIG. 2, measuring apparatus 100 is wrapped around calf 202 such that first surface 102 faces away from calf 202 and a loop is formed around calf 202. Measuring apparatus 100 may be moved up and down calf 202 in order to find the portion of calf 202 having the largest circumference. The likelihood that the patient has peripheral arterial disease can be obtained by reading the markings on first surface 202 at the point where starting point 106 of measuring apparatus 100 intersects second surface 104. For example, if the point where starting point 106 intersects second surface 104 is within first segment 110, it may be determined that the patient has a low likelihood of peripheral arterial disease. If the point where starting point 106 intersects second surface 104 is within second segment 112, it may be determined that the patient has a medium likelihood of peripheral arterial disease. If the point where starting point 106 intersects second surface 104 is within third segment 114, it may be determined that the patient has a high likelihood of peripheral arterial disease. In the example shown in FIG. 2, measuring apparatus 100 indicates that the patient has medium likelihood of having peripheral arterial disease.

Figure 3:
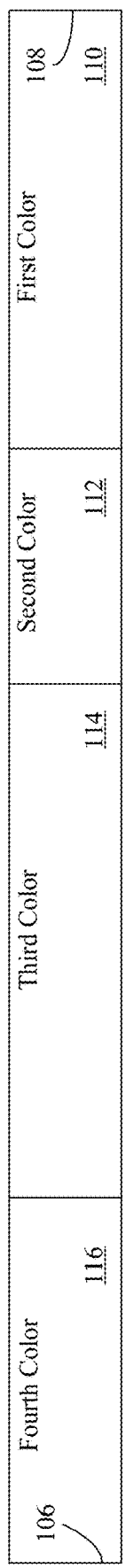
FIG. 3 shows a block diagram of a measuring apparatus having a first surface that is color-coded in accordance with an embodiment.

In accordance with an embodiment, segments 110, 112, 114, and 116 may be defined by different colors (in addition to or in lieu of using segment markers 118, 120, and 122), thereby forming a color-coded measuring apparatus. For example, FIG. 3 is a block diagram of measuring apparatus 100 in which first surface 102 is color-coded in accordance with an embodiment. As shown in FIG. 3, first segment 110 is defined by the portion of first surface 102 that has a first color (e.g., green), second segment 112 is defined by the portion of first surface 102 that has a second color (e.g., yellow or orange), third segment 114 is defined by the portion of first surface 102 that has a third color (e.g., red), and fourth segment 116 is defined by the portion of first surface 102 that has a fourth color (e.g., white). It is noted that the colors described above are merely exemplary and that each of segments 110, 112, 114, and 116 may be any color, including a range of gray shades (i.e., grayscale) or other shades of a single or multiple colors.

Figure 4:
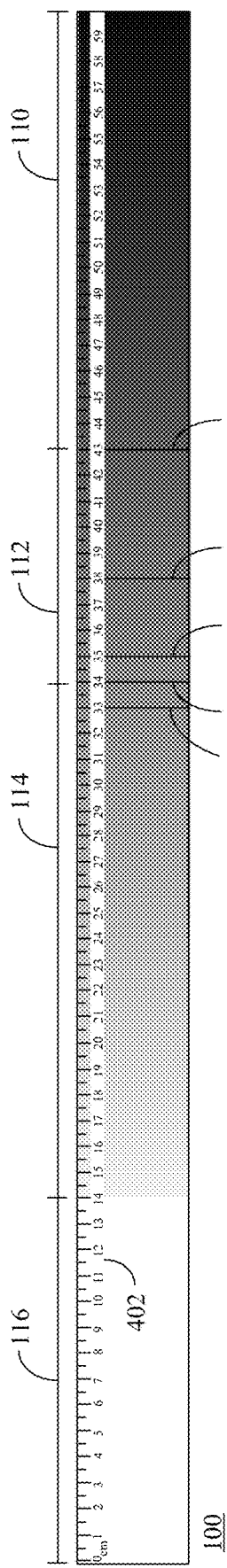
FIG. 4 shows a block diagram of a measuring apparatus having a first surface that is color-coded using gradients in accordance with an embodiment.

In accordance with an embodiment, the color of each segments 110, 112, 114, and 116 may be represented as a gradient. For example, FIG. 4 is a block diagram of measuring apparatus 100 in which first surface 102 is color-coded using gradients in accordance with an embodiment. For instance, first segment 110 may be defined by the portion of first surface 102 having a first gradient being based on first color (e.g., green), second segment 112 may be defined by the portion of first surface 102 having a second gradient being based on second color (e.g., yellow or orange), and third segment 114 may be defined by the portion of first surface 102 having a third gradient being based on a third color (e.g., red). Fourth segment 116 may be defined by the portion of first surface 102 having no gradient and may simply be a solid color (e.g., white). It is noted that the gradients described above are merely exemplary and that each of segments 110, 112, 114, and 116 may have gradients based on any color, including a range of gray shades (i.e., grayscale).

Measuring apparatus 100 may further include one or more additional features printed thereupon. For example, as further shown in FIG. 4, first surface 102 may include a set of length markings 402 that divide first surface 102 by standard units of length (e.g., centimeters). It is noted that while FIG. 4 depicts the standard unit of length to be centimeters, any standard of unit of length may be used (e.g., inches, millimeters, etc.). As also shown in FIG. 4, first surface 102 may also include a first indicator 404, a second indicator 406, a third indicator 408, a fourth indicator 410, and/or a fifth indicator 412 printed thereupon. First indicator 404 may represent the mean of patients that do not have peripheral arterial disease. Second indicator 406 may represent the standard error of mean of patients without peripheral arterial disease. Third indicator 408 may represent the mean of patients that have peripheral arterial disease. Fourth indicator 410 may represent the mean plus the standard deviation of the patients that have peripheral arterial disease. Fifth indicator 412 may represent the mean minus the standard deviation of the patients that have peripheral arterial disease. The above-described means, standard error of means and standard deviations may be based on the statistical analysis performed on data associated with a plurality of patients as described above.

In an embodiment, second surface 104 (as shown in FIG. 1B) may include the same color scheme as shown in FIGS. 3 and 4 and/or each of markings 402, 404, 406, 408, 410 and/or 412 shown in FIG. 4, may include instructions for using measuring apparatus 100, and/or may be marked and/or colored/shaded in other ways.

B. Screening Application

As described above in Subsection II.A, a measuring apparatus may be used to assess the likelihood as to whether a patient has peripheral arterial disease. The assessment may be further refined using additional data regarding the patient. For example, the data may be analyzed by an application to make a refined assessment as to whether the patient has peripheral arterial disease.

Figure 5:
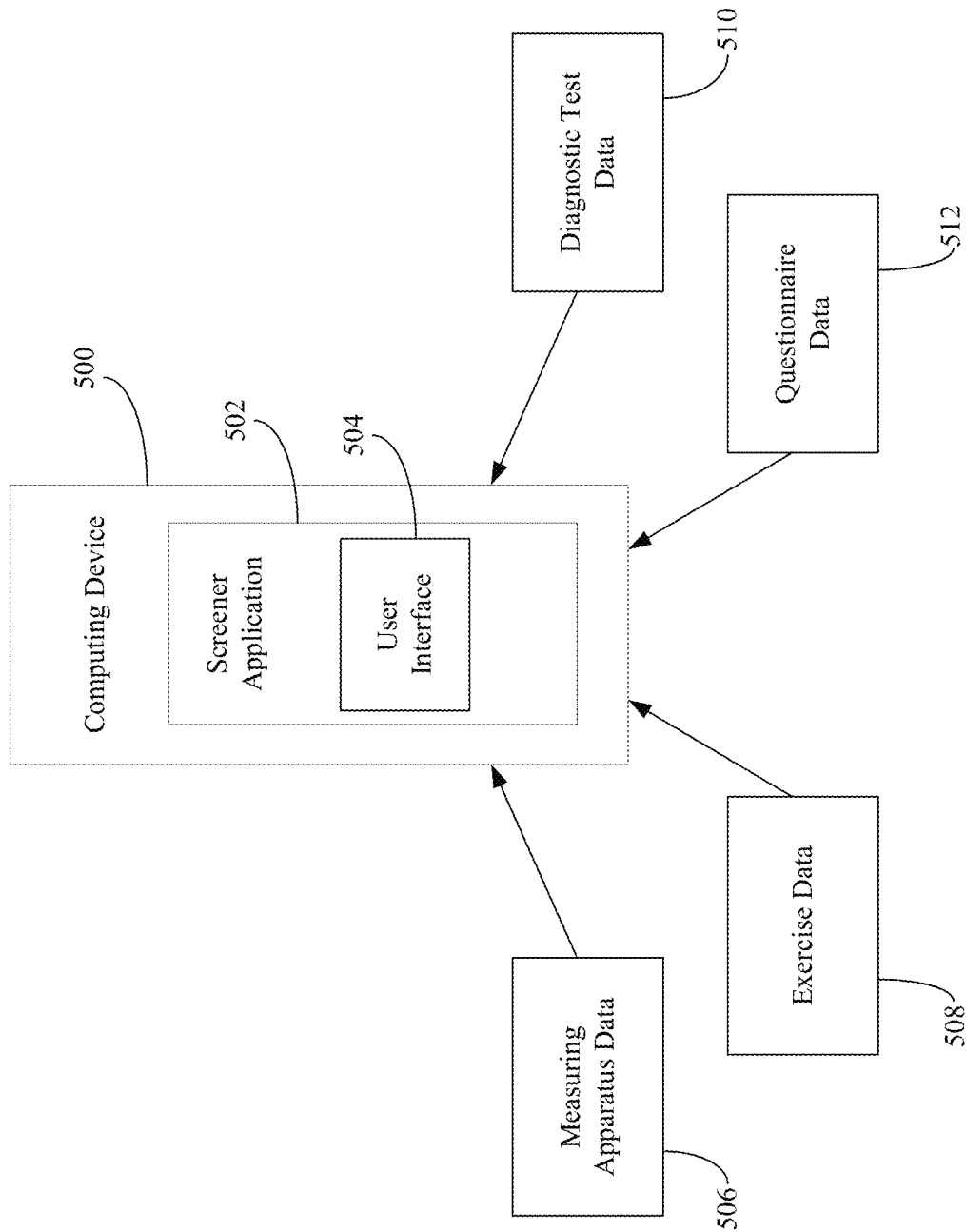
FIG. 5 shows a block diagram of a computing device configured to assess whether a patient has peripheral arterial disease based on various types of data in accordance with an embodiment.

FIG. 5 is a block diagram of a computing device 500 configured to assess whether a patient has peripheral arterial disease based on various types of data in accordance with an example embodiment. Computing device 500 may be any type of stationary or mobile computing device, including a desktop computer (e.g., a personal computer, etc.), a mobile computer or computing device (e.g., a Palm® device, a RIM Blackberry® device, a personal digital assistant (PDA), a laptop computer, a notebook computer, a tablet computer (e.g., an Apple iPad™), a smart phone (e.g., an Apple iPhone, a Google Android™ phone, a Microsoft Windows® phone, etc.), or other type of computing device. As shown in FIG. 5, computing device 500 includes a screener application 502.

Screener application 502 may be a software application that executes in hardware, and is configured to receive data associated with a patient and make an assessment as to whether the patient has peripheral arterial disease based on the data. The data includes one or more of measuring apparatus data 506, exercise data 508, diagnostic test data 510 and/or questionnaire data 512. Screener application 502 may include a user interface 504 that enables a user to enter in measuring apparatus data 506, exercise data 508, diagnostic test data 510 and/or questionnaire data 512.

Measurement apparatus data 506 may comprise one or more measurements taken using the measuring apparatus described above in Subsection A. For example, the measurement(s) may include the determined likelihood that the patient has peripheral arterial disease (e.g., a low likelihood, a medium likelihood, or a high likelihood) and/or the calf circumference (e.g., in centimeters). The determined likelihood and/or calf circumference is provided to screener application 502 via user interface 504.

Exercise data 508 may comprise data associated with one or more exercises that the patient has performed. For example, it has been observed that peripheral arterial disease limits the walking ability of patients. A six-minute walk test has been shown to be a reliable and a reproducible method of assessing this limitation. The six-minute walk test assesses the distance that a patient walks at a normal pace during six minutes. Exercise data 508 may include results of a patient's six-minute walk test (i.e., the distance traveled (e.g., the number of feet, meters, etc.) in six minutes). The distance traveled may be indicative of whether the patient has peripheral arterial disease. For example, if the patient is able to walk less than a predetermined threshold (e.g., 300 meters) within six minutes, this may be an indication, or a determination, that the patient may have peripheral arterial disease. It is noted that the predetermined threshold is exemplary, and other thresholds may be used. It is further noted that the threshold may vary depending on certain characteristics of the patient (e.g., age, weight, etc.). The distance traveled is provided to screener application 502 via user interface 504.

Diagnostic test data 510 may comprise data associated with one or more diagnostic tests performed on the patient. One such exam is a toe brachial index exam. It has been observed that patients with peripheral arterial disease have blockages in the arteries to the extremities. Thus, pressure in the involved extremity would be lower than that in the uninvolved extremity. Calcification of the patient's medium-sized arteries makes pressure measurement unreliable in the involved blood vessels. Toe pressure measurement avoids this error. Thus, a ratio of the toe pressure to the arm pressure (also referred to as the toe brachial index (TBI)) provides a measure of the presence (or absence) of peripheral arterial disease. The toe and/or arm pressure may be determined using known techniques, such, but not limited to, a continuous wave Doppler, a sphygmomanometer, and/or pressure cuffs. The TBI may be determine before and/or after the six-minute walk test. A TBI that is lower than 0.7 or higher than 1.3 may indicate the presence of peripheral arterial disease. Additionally, an absolute toe pressure less than 50 millimeters of mercury (mmHg) may indicate critical limb ischemia (if a leg wound forms, it may not heal). The determined TBI(s) are provided to screener application 502 via user interface 504.

Questionnaire data 512 may comprise data collected via one or more questions provided to the patient that are directed to determining the severity of various patient symptoms. Such questions may inquire about the severity of pain and/or the numbness in the patient's leg and/or foot while walking, the severity of weakness or tiredness in the patient's leg and/or foot, the severity of pain in the patient's leg and/or foot while resting, whether the patient has had any pain in the leg and/or foot while resting, etc. The level of severity for each of the symptoms indicated by the patient may be indicative of peripheral arterial disease (where the more severe the symptoms, the more likely the patient has peripheral arterial disease). The answers to the questions are provided to screener application 502 via user interface 504.

Screener application 502 may be configured to use the above-described measuring apparatus data 506, exercise data 508, diagnostic test data 510 and/or questionnaire data 512 to provide a comprehensive report of the patient and make an assessment as to whether the patient has peripheral arterial disease and the severity thereof. The severity of peripheral arterial disease may be based on a combination of the data that indicates whether the patient likely has peripheral arterial disease. For example, if each of measuring apparatus data 506, exercise data 508, diagnostic test data 510 and/or questionnaire data 512 are indicative of the patient having peripheral arterial disease, then screener application 502 may determine that patient has the most severe case of peripheral arterial disease. Conversely, if none of measuring apparatus data 506, exercise data 508, diagnostic test data 510 and/or questionnaire data 512 are indicative of the patient having peripheral arterial disease, screener application 502 may determine that the patient does not have peripheral arterial disease. A weighting of the various data may be combined to generate an overall assessment, which may be compared to one or more threshold levels to indicate the patient does have or does not have peripheral arterial disease, or provide some likelihood in between (e.g., medium likelihood). Severity of peripheral arterial disease may be adjudicated using non-invasive physiological measurements, which are important predictor of outcome than anatomical angiographic measurements. Machine learning techniques may be used and refined to further categorize likelihood and severity of peripheral arterial disease.

C. Prescribed Walking Program Compliance

After a determination is made that a patient likely has peripheral arterial disease, a healthcare practitioner may prescribe a walking program for the patient to follow. The goal of the walking program is to mitigate the effects of peripheral arterial disease. The patient may carry a computing device that executes a software application that tracks the distance the patient has travelled. The distance travelled may be transmitted to a computing device associated with the healthcare practitioner. The healthcare practitioner's computing device may assess whether the patient has complied with the prescribed walking program based on the received distance travelled. If it is determined that the patient has not complied with the prescribed walking program, the computing device may transmit escalating reminders to the patient that increase in severity. For example, the first time the patient does not comply with the prescribed walking program, the patient may receive a message via the application that tracks the distance travelled by the user reminding the patient to comply with the prescribed walking program (e.g., "Don't forget to walk 1000 steps today"). The second time the patient does not comply with the prescribed walking program, the patient may receive a more urgent message (e.g., text message) reminding the patient to comply with the prescribed walking program ("e.g., "URGENT: REFUSAL TO COMPLY WITH YOUR PRESCRIBED WALKING PROGRAM MAY WORSEN YOUR SYMPTOMS!!!"). Thereafter, the patient may receive a phone call from the healthcare practitioner to remind the patient to comply with the prescribed walking program, and ultimately, would receive a phone call from the healthcare practitioner to schedule an appointment therewith.

Figure 6:
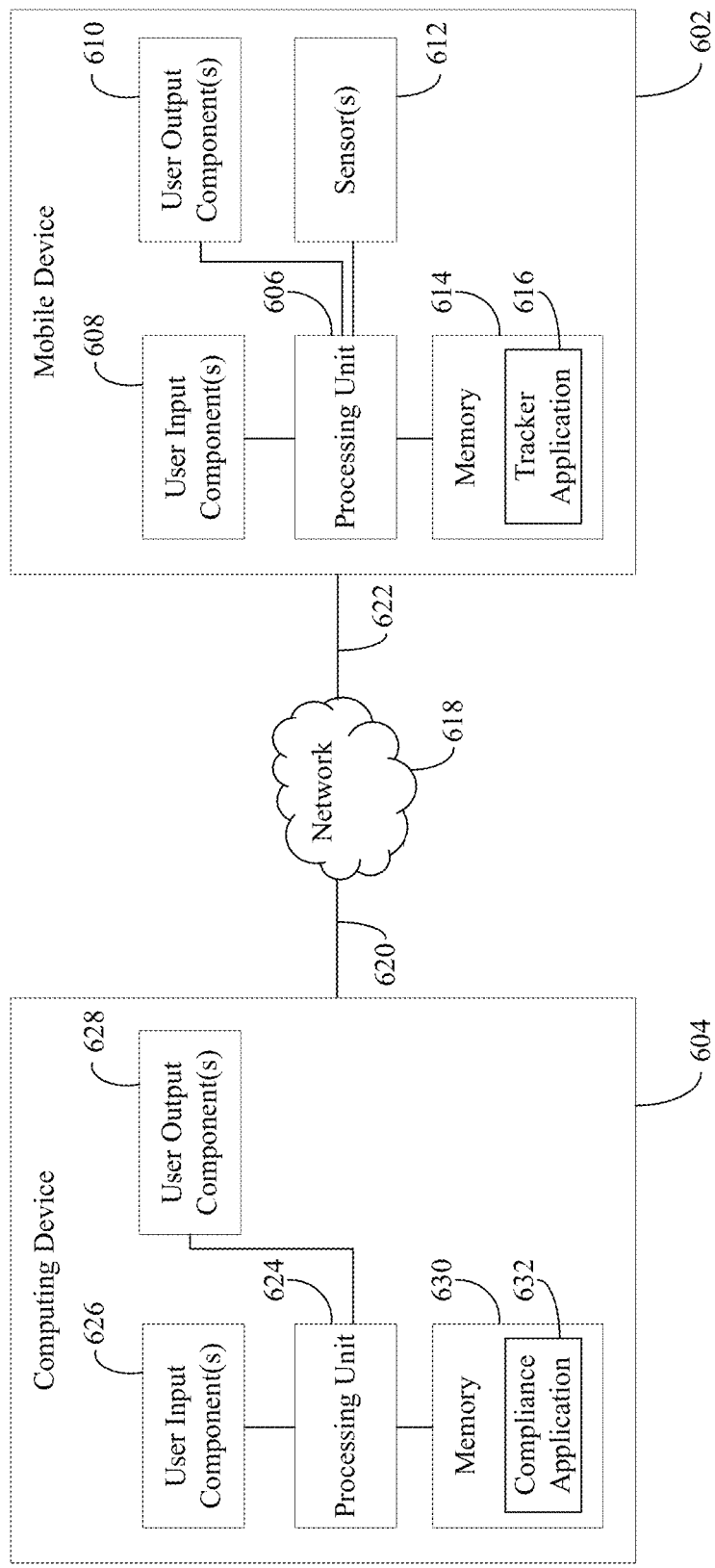
FIG. 6 shows a block diagram of a system for tracking compliance of a prescribed walking program in accordance with an embodiment.

FIG. 6 is a block diagram of a system for tracking compliance of a prescribed walking program in accordance with an embodiment. As shown in FIG. 6, system 600 includes a mobile device 602 and a computing device 604. Mobile device 602 and computing device 604 may each may comprise any of a wide variety of portable electronic devices mentioned herein or otherwise known, including but not limited to a smart phone, a tablet computer, a laptop computer, a wearable computing device, a wearable fitness device, a pedometer, a personal media player, or the like. Mobile device 602 and computing device 604 are each presented herein by way of example only.

As shown in FIG. 6, mobile device 602 includes a processing unit 606. Processing unit 604 comprises a central processing unit (CPU), a microprocessor, a multi-core processor, or other integrated circuit that is configured to execute computer program instructions that are retrieved from memory (e.g., memory 614), thereby causing certain operations to be performed. As further shown in FIG. 6, processing unit 606 is connected to one or more user input components 608, one or more user output component 610, one or more sensors 612, and a memory 614.

User input component(s) 608 may comprise one or more of a touch screen, keypad, button, microphone, camera, or other component suitable for enabling a user to provide input to mobile device 602. User output component(s) 610 may comprise one or more of a display, audio speaker, haptic feedback element, or other component suitable for providing output to a user of mobile device 602.

Sensor(s) 612 may comprise an accelerometer and/or a gyroscope. The accelerometer may be configured to measure acceleration forces. In an embodiment, the accelerometer comprises a 3-axis accelerometer that is configured to measure acceleration along each of three orthogonal axes of a right-handed mobile device reference frame. The three axes may be denoted the x-axis, the y-axis, and the z-axis. In an embodiment in which mobile device 602 comprises a mobile phone having a generally rectangular display on one side thereof, the x-axis may run along the short side of the display, the y-axis may run along the long side of the display, and the z-axis may run perpendicular to and out of the front of the display. However, other mobile device reference frames may be used. Each acceleration measurement may be represented in meters per second squared ($m/s^2$) or other suitable unit of measurement. The gyroscope may be configured to measure orientation of mobile device 602. In an embodiment, the gyroscope comprises a 3-axis MEMS gyroscope that is configured to measure a rate of rotation around each of the axes of the aforementioned mobile device reference frame. Each gyroscope measurement may be represented in radians per second (rad/s) or other suitable unit of measurement.

Memory 614 comprises one or more volatile or non-volatile memory devices that are operable to store computer program instructions (also referred to herein as computer program logic). These computer program instructions may be retrieved from memory 614 and executed by processing unit 606 in a well-known manner to cause processing unit 606 to perform certain operations.

As further shown in FIG. 6, memory 614 stores tracker application 616. Tracker application 616 comprises computer program instructions that, when executed by processing unit 606, causes processing unit 606 to perform an algorithm for determining a number of steps taken or a distance travelled by a patient within a predetermined time period using data collected from sensor(s) 612. Based on the teachings provided herein, persons skilled in the relevant art(s) will appreciate that the method for determining a distance travelled by a patient predetermined time period can be implemented by other devices and systems as well.

Sensor data indicative of the number of steps and/or distance travelled may be provided to computing device 604 via network 618. Network 618 may be a LAN (local area network), a WAN (wide area network), or any combination of networks, such as the Internet. Computing device 604 is coupled to network 618 through a communication link 620, and mobile device 602 is coupled with network 618 through a communication link 622. Communication links 620 and 622 may each include wired and/or wireless links. Examples of communication links 620 and 622 include IEEE 802.11 wireless LAN (WLAN) wireless links, Worldwide Interoperability for Microwave Access (Wi-MAX) links, cellular network links, wireless personal area network (PAN) links (e.g., Bluetooth™ links), Ethernet links, USB (universal serial bus) links, etc.

Computing device 604 may be a device associated with a healthcare practitioner. For example, computing device 604 may be located at the office, hospital, etc. of the healthcare practitioner. As shown in FIG. 6, computing device 604 may include a processing unit 624, input component(s) 626, user output component(s) 628, and a memory 630. Processing unit 624, user input component(s) 626, user output component(s) 628, and memory 630 are examples of processing unit 606, user input component(s) 608, user output component(s) 610, and memory 614, and therefore, may operate in a similar manner as described above. As shown in FIG. 6, memory 630 stores a compliance application 632. Compliance application 632 comprises computer program instructions that, when executed by processing unit 624, causes processing unit 624 to perform an algorithm for determining whether a patient has complied with a walking program prescribed by the healthcare practitioner based on the sensor data provided by tracker application 616.

For example, compliance application 632 may provide a user interface that enables a healthcare practitioner to enter in a walking program (e.g., using user input component(s) 626) that a patient is to comply with. Examples of a walking program may include, but are not limited to, walking 1000 meters in a day, 5000 meters in a week, etc. Compliance program 632 may compare the number of steps and/or distance travelled within the predetermined time period indicated by the sensor data received from mobile device 602 to the walking program and determine whether the patient has complied with the walking program. If compliance program 632 determines that the patient has not complied with the prescribed walking program, compliance program may transmit escalating reminders to the patient that increase in severity if the patient continues to not comply with the prescribed walking program. For example, the first time the patient does not comply with the prescribed walking program, compliance program 632 may transmit a command to tracker application 616 (e.g., via network 618) that causes tracker application 616 to display a message reminding the patient to comply with the walking program. The second time the patient does not comply with the prescribed walking program, compliance program 632 may cause a text message (e.g., a short messaging system (SMS) message) to be transmitted to mobile device 602 and/or other another computing device associated with the patient (e.g., the patient's smart phone, tablet, etc.). Alternatively, compliance program 632 may display a notification via computing device 604 (e.g., using user output component(s) 628) that indicates that the healthcare practitioner should transmit a text message (e.g., by using the healthcare practitioner's phone) to mobile device 602 and/or another computing device associated with the patient. The third time the patient does not comply with the prescribed walking program, compliance program 632 may display a notification via computing device 604 that indicates that the healthcare practitioner should call the patient to remind the patient to comply with the prescribed walking program. The fourth time the patient does not comply with the prescribed walking program, compliance program 632 may display a notification via computing device 604 that indicates that the healthcare practitioner should call the patient to schedule an appointment for the patient to visit the healthcare practitioner. It is noted that the reminders described do not necessarily have to be transmitted to the patient each time the patient fails to comply with the prescribed walking program. Instead, a reminder may be transmitted every Nth time a patient fails to comply with the prescribed walking program, where N is any integer greater than one. Furthermore, different numbers and types of reminders may be used in other embodiments.

Figure 7:
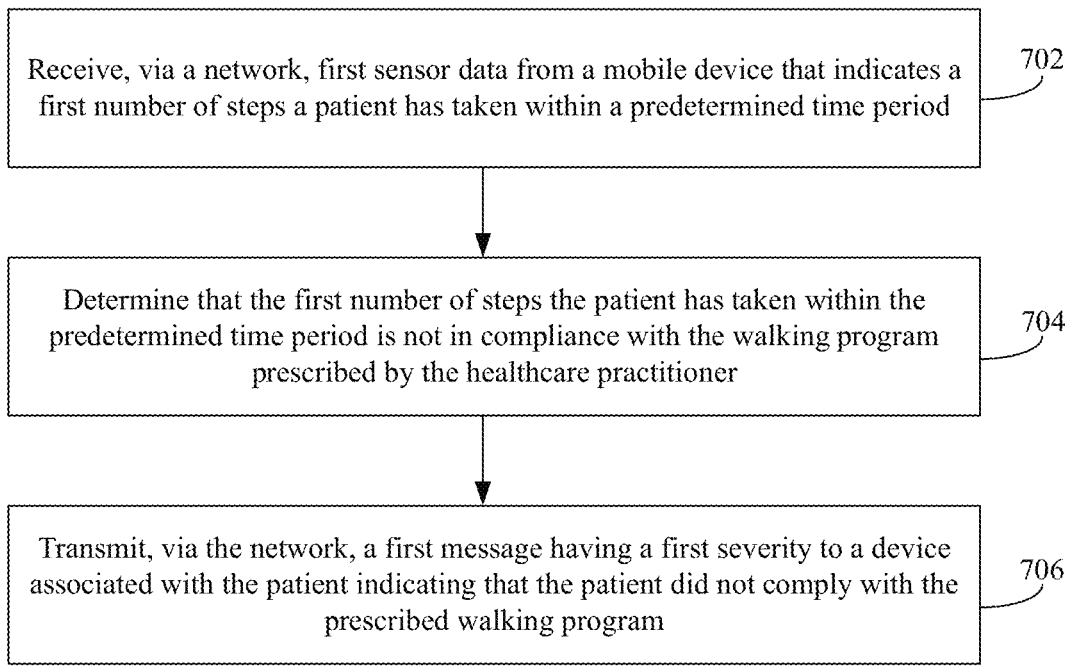
FIG. 7 depicts a flowchart of a method for tracking compliance of a prescribed walking program in accordance with an embodiment.
Figure 8:
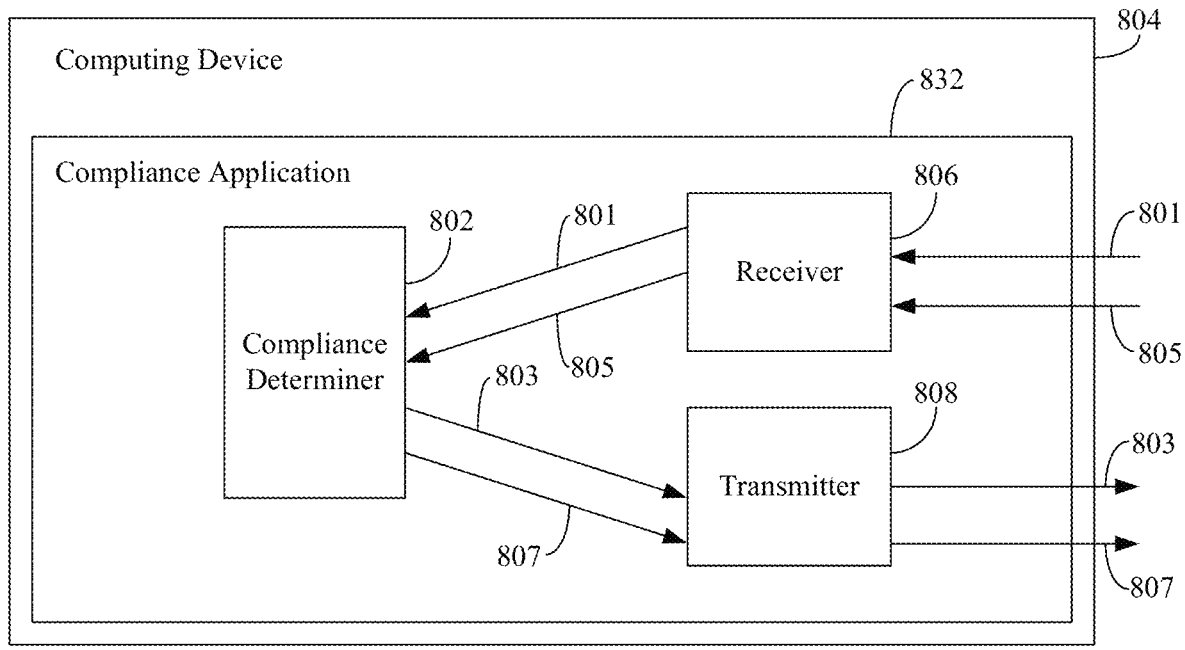
FIG. 8 shows a block diagram of a computing device that includes a compliance application in accordance with an embodiment.

Accordingly, in embodiments, compliance of a prescribed walking program may be tracked in many ways. For instance, FIG. 7 shows a flowchart 700 of a method for tracking compliance of a prescribed walking program in accordance with an embodiment. The method of flowchart 700 may be implemented by a computing device 804 shown in FIG. 8. FIG. 8 depicts a block diagram 800 of computing device 804 in accordance with an embodiment. Computing device 804 is an example of computing device 604 described above with reference to FIG. 6. As shown in FIG. 8, computing device 804 includes a compliance application 832. Compliance application 832 is an example of compliance application 632 described above with reference to FIG. 6. Compliance application 832 includes compliance determiner 802, a receiver 806, and a transmitter 808. Other structural and operational embodiments will be apparent to persons skilled in the relevant art(s) based on the following discussion regarding flowchart 700 and computing device 804.

Flowchart 700 begins with step 702. At step 702, first sensor data is received via a network from a mobile device that indicates a first number of steps a patient has taken within a predetermined time period. For example, with reference to FIG. 8, receiver 806 may receive first sensor data 801 via a network (e.g., network 618, as shown in FIG. 6) from a mobile device (e.g., mobile device 602, as shown in FIG. 6). First sensor data 801 may indicate a first number of steps a patient has taken within a predetermined time period. First sensor data 801 is provided to compliance determiner 802.

At step 704, a determination is made that the first number of steps the patient has taken within the predetermined time period is not in compliance with the walking program prescribed by the healthcare practitioner. For example, with reference to FIG. 8, compliance determiner 802 determines that the first number of steps the patient has taken within the predetermined time period is not in compliance with the walking program prescribed by the healthcare practitioner.

At step 706, a first message having a first severity is transmitted via the network to a device associated with the patient indicating that the patient did not comply with the prescribed walking program. For example, with reference to FIG. 8, compliance determiner 802 generates a first message 803 having a first severity that indicates that the patient did not comply with the prescribed walking program. First message 803 is provided to transmitter 808. Transmitter 808 transmits first message 803 to a device associated with the patient via the network (e.g., network 618).

In accordance with one or more embodiments, the device associated with the patient is the mobile device (e.g., mobile device 602, as shown in FIG. 6).

In accordance with one or more embodiments, the device associated with the patient is a computing device associated with the user other than the mobile device (e.g., the patient's smart phone, tablet, etc.).

In accordance with one or more embodiments, the first message is configured to be displayed via an application executing on the device associated with the patient. For example, with reference to FIG. 6, the first message is configured to be displayed via tracker application 616 executing on mobile device 602. For instance, tracker application 616 may cause user output component(s) 610 to display the first message.

In accordance with one or more embodiments, the prescribed walking program is based on a distance that the patient is able to walk within the predetermined time period.

In accordance with an embodiment, computing device 804 uses a single transceiver rather than a separate transmitter and receiver (i.e., receiver 806 and transmitter 808) for performing communication via the network.

In some example embodiments, one or more of steps 702, 704, and/or 706 of flowchart 700 may not be performed. Moreover, operations in addition to or in lieu of steps 702, 704, and/or 706 may be performed. Further, in some example embodiments, one or more of steps 702, 704, and/or 706 may be performed out of order, in an alternate sequence, or partially (or completely) concurrently with each other or with other operations.

Figure 9:
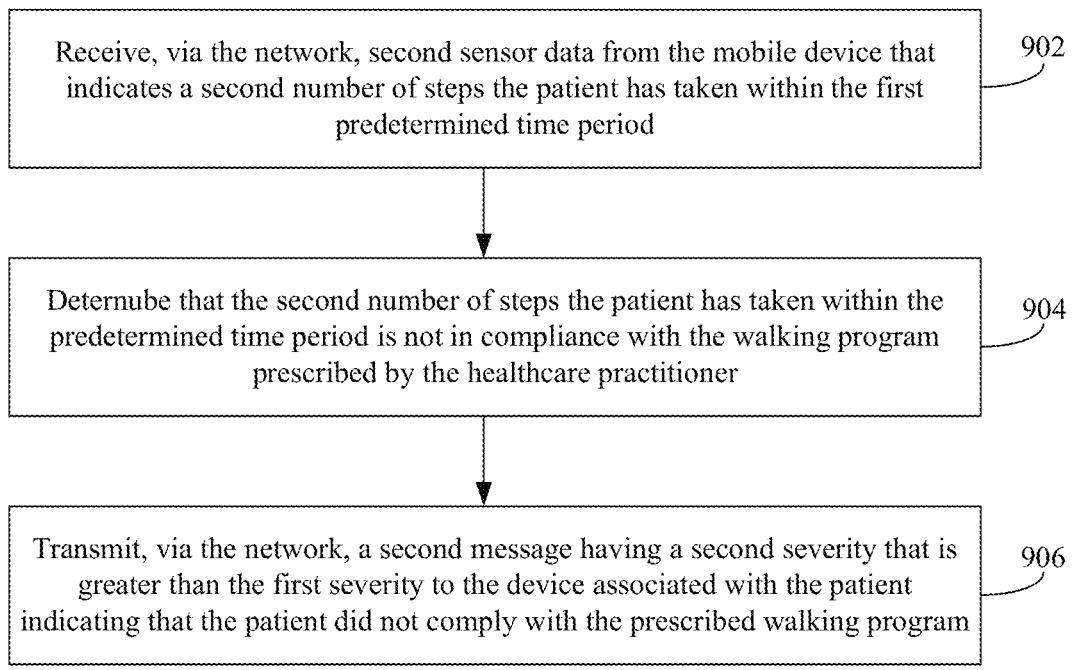
FIG. 9 depicts a flowchart of a method for transmitting messages of increasing severity as a patient continues to not comply with a prescribed walking program in accordance with an embodiment.

In accordance with one or more embodiments, compliance application 832 is configured to transmit messages of increasing severity as the patient continues to not comply with the prescribed walking program. For instance, FIG. 9 shows a flowchart 900 of a method for transmitting messages of increasing severity as the patient continues to not comply with a prescribed walking program in accordance with an embodiment. The method of flowchart 900 may be implemented by a computing device 804 shown in FIG. 8. Accordingly, FIG. 9 will be described with continued reference to FIG. 8. Other structural and operational embodiments will be apparent to persons skilled in the relevant art(s) based on the following discussion regarding flowchart 900 and computing device 804.

Flowchart 900 begins with step 902. At step 902, second sensor data is received via the network from the mobile device that indicates a second number of steps a patient has taken within the predetermined time period. For example, with reference to FIG. 8, receiver 806 may receive second sensor data 805 via a network (e.g., network 618, as shown in FIG. 6) from a mobile device (e.g., mobile device 602, as shown in FIG. 6). Second sensor data 805 may indicate a second number of steps a patient has taken within the predetermined time period. First sensor data 805 is provided to compliance determiner 802.

At step 804, a determination is made that the second number of steps the patient has taken within the predetermined time period is not in compliance with the walking program prescribed by the healthcare practitioner. For example, with reference to FIG. 8, compliance determiner 802 determines that the second number of steps the patient has taken within the predetermined time period is not in compliance with the walking program prescribed by the healthcare practitioner.

At step 806, a second message having a second severity that is greater than the first severity is transmitted via the network to the device associated with the patient indicating that the patient did not comply with the prescribed walking program. For example, with reference to FIG. 8, compliance determiner 802 generates a second message 807 having a second severity that is greater than the first severity indicates that the patient did not comply with the prescribed walking program. Second message 807 is provided to transmitter 808. Transmitter 808 transmits second message 807 to a device associated with the patient via the network (e.g., network 618).

In accordance with one or more embodiments, the second message is a text message.

In some example embodiments, one or more of steps 902, 904, and/or 906 of flowchart 900 may not be performed. Moreover, operations in addition to or in lieu of steps 902, 904, and/or 906 may be performed. Further, in some example embodiments, one or more of steps 902, 904, and/or 906 may be performed out of order, in an alternate sequence, or partially (or completely) concurrently with each other or with other operations.

D. Additional Embodiments

1. Tissue Loss Determination

Peripheral arterial disease is known to cause tissue loss. It has been observed that such tissue loss can result in the loss of calf circumference. The measuring apparatus described above in Subsection A may be also be used to quantify tissue loss. For example, the measuring apparatus may be used to periodically measure the calf circumference. If the measurements indicate that the measured calf circumference decreases over time, then it may be determined that the patient has suffered from tissue loss.

2. Fall Risk Assessment

A leading cause of death in the United States among the elderly is falling. One contributed factor may be a smaller calf circumference, along with other factors, such as visual acuity, age of shoes and certain environment issues (e.g., loose rugs, a lack of handicap handles at the home, etc.). In accordance with an embodiment, screener application 502, as described above with reference to FIG. 5, may be configured to determine the risk of the patient falling based on the measured calf circumference and the additional factors described above. For example, the patient may be required to fill out a questionnaire asking the patient to identify the above-described factors. The patient's answers may be provided to screener application 502 as questionnaire data 512, along with measuring apparatus data 506 (i.e., measured calf circumference). Screener application 502 may be configured to assess the risk of the patient falling based on questionnaire data 512 and/or measuring apparatus data 506 and provide a score of the risk of the patient falling accordingly.

III. Further Example Embodiments

A device, as defined herein, is a machine or manufacture as defined by 35 U.S.C. § 101. That is, as used herein, the term "device" refers to a machine or other tangible, manufactured object and excludes software and signals. Devices may include digital circuits, analog circuits, or a combination thereof. Devices may include integrated circuits (ICs), one or more processors (e.g., central processing units (CPUs), microprocessors, digital signal processors (DSPs), etc.) and/or may be implemented with any semiconductor technology, including one or more of a Bipolar Junction Transistor (BJT), a heterojunction bipolar transistor (HBT), a metal oxide field effect transistor (MOSFET) device, a metal semiconductor field effect transistor (MESFET) or other transconductor or transistor technology device. Such devices may use the same or alternative configurations other than the configuration illustrated in embodiments presented herein.

Techniques and embodiments, including methods, described herein may be implemented in hardware (digital and/or analog) or a combination of hardware and software and/or firmware. Techniques described herein may be implemented in one or more components. Embodiments may comprise computer program products comprising logic (e.g., in the form of program code or instructions as well as firmware) stored on any computer useable storage medium, which may be integrated in or separate from other components. Such program code, when executed in one or more processors, causes a device to operate as described herein. Devices in which embodiments may be implemented may include storage, such as storage drives, memory devices, and further types of computer-readable media. Examples of such computer-readable storage media include, but are not limited to, a hard disk, a removable magnetic disk, a removable optical disk, flash memory cards, digital video disks, random access memories (RAMs), read only memories (ROM), and the like. In greater detail, examples of such computer-readable storage media include, but are not limited to, a hard disk associated with a hard disk drive, a removable magnetic disk, a removable optical disk (e.g., CDROMs, DVDs, etc.), zip disks, tapes, magnetic storage devices, MEMS (microelectromechanical systems) storage, nanotechnology-based storage devices, as well as other media such as flash memory cards, digital video discs, RAM devices, ROM devices, and the like. Such computer-readable storage media may, for example, store computer program logic, e.g., program modules, comprising computer executable instructions that, when executed, provide and/or maintain one or more aspects of functionality described herein with reference to the figures, as well as any and all components, steps and functions therein and/or further embodiments described herein.

Computer readable storage media are distinguished from and non-overlapping with communication media. Communication media embodies computer-readable instructions, data structures, program modules or other data in a modulated data signal such as a carrier wave. The term "modulated data signal" means a signal that has one or more of its characteristics set or changed in such a manner as to encode information in the signal. By way of example, and not limitation, communication media includes wired media as well as wireless media such as acoustic, RF, infrared and other wireless media. Example embodiments are also directed to such communication media.

The peripheral arterial disease assessment, fall risk assessment and/or the tracking of a prescribed walking program compliance embodiments and/or any further systems, sub-systems, and/or components disclosed herein may be implemented in hardware (e.g., hardware logic/electrical circuitry), or any combination of hardware with software (computer program code configured to be executed in one or more processors or processing devices) and/or firmware.

Figure 10:
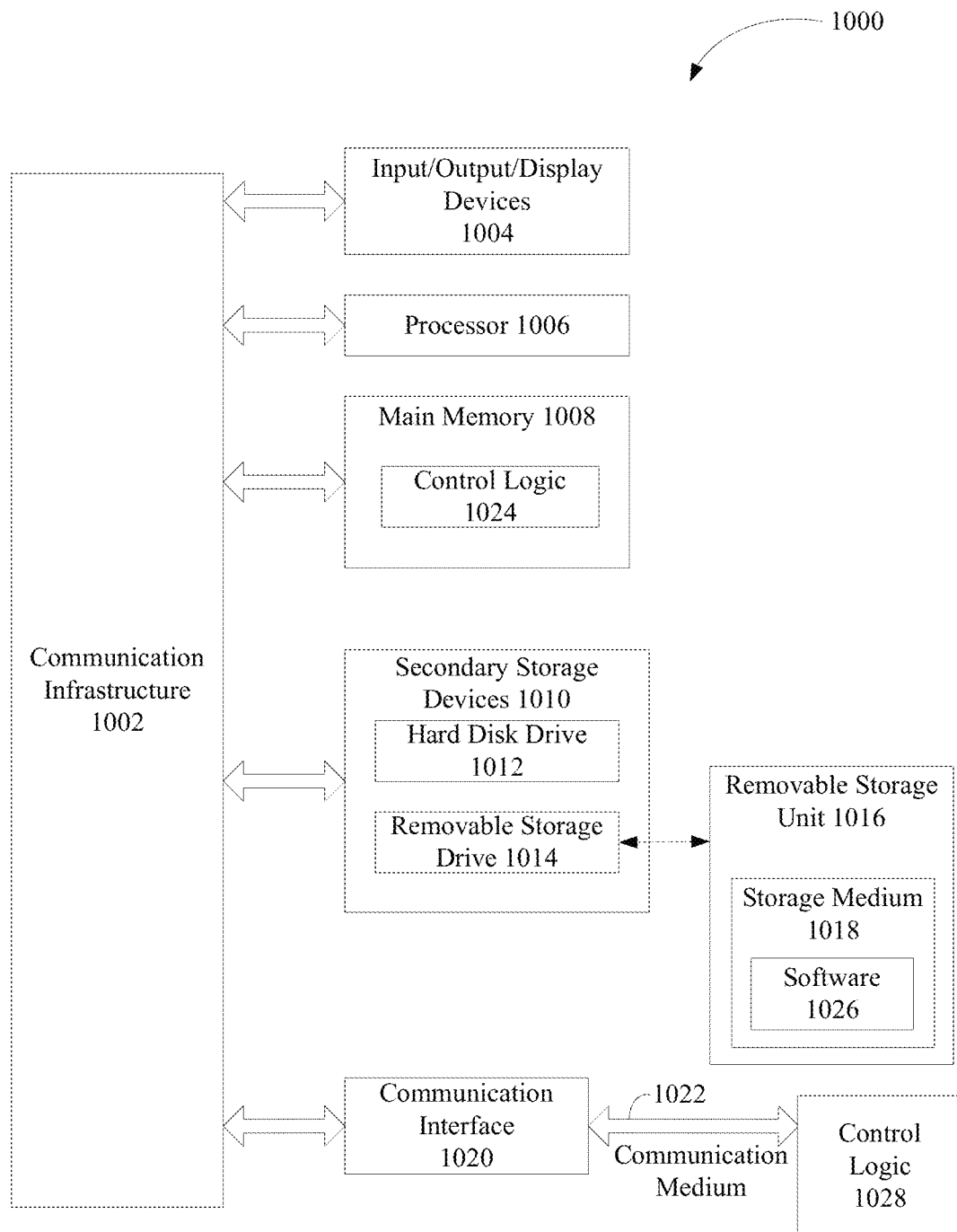
FIG. 10 is a block diagram of a computer system in accordance with an embodiment.

The embodiments described herein, including systems, methods/processes, and/or apparatuses, may be implemented using well known processing devices, telephones (smart phones and/or mobile phones), servers, electronic devices (e.g., consumer electronic devices) and/or, computers, such as a computer 1000 shown in FIG. 10. It should be noted that computer 1000 may represent communication devices, processing devices, servers, and/or traditional computers in one or more embodiments. For example, computing device 500, screener application 502, tracker application 616, compliance application 632, mobile device 602, computing device 604, computing device 804, and/or compliance application 832 (as described above with reference to FIGS. 5, 6, and 8, respectively), and/or any of the sub-systems, components or sub-components respectively contained therein, may be implemented using one or more computers 1000.

Computer 1000 can be any commercially available and well known communication device, processing device, and/or computer capable of performing the functions described herein, such as devices/computers available from International Business Machines®, Apple®, Sun®, HP®, Dell®, Cray®, Samsung®, Nokia®, etc. Computer 1000 may be any type of computer, including a desktop computer, a server, etc.

Computer 1000 includes one or more processors (also called central processing units, or CPUs), such as a processor 1006. Processor 1006 is connected to a communication infrastructure 1002, such as a communication bus. In some embodiments, processor 1006 can simultaneously operate multiple computing threads.

Computer 1000 also includes a primary or main memory 1008, such as random access memory (RAM). Main memory 1008 has stored therein control logic 1024 (computer software), and data.

Computer 1000 also includes one or more secondary storage devices 1010. Secondary storage devices 1010 include, for example, a hard disk drive 1012 and/or a removable storage device or drive 1014, as well as other types of storage devices, such as memory cards and memory sticks. For instance, computer 1000 may include an industry standard interface, such a universal serial bus (USB) interface for interfacing with devices such as a memory stick. Removable storage drive 1014 represents a floppy disk drive, a magnetic tape drive, a compact disk drive, an optical storage device, tape backup, etc.

Removable storage drive 1014 interacts with a removable storage unit 1016. Removable storage unit 1016 includes a computer useable or readable storage medium 1018 having stored therein computer software 1026 (control logic) and/or data. Removable storage unit 1016 represents a floppy disk, magnetic tape, compact disk, DVD, optical storage disk, or any other computer data storage device. Removable storage drive 1014 reads from and/or writes to removable storage unit 1016 in a well-known manner.

Computer 1000 also includes input/output/display devices 1004, such as touchscreens, LED and LCD displays, monitors, keyboards, pointing devices, etc.

Computer 1000 further includes a communication or network interface 1018. Communication interface 1020 enables computer 1000 to communicate with remote devices. For example, communication interface 1020 allows computer 1000 to communicate over communication networks or mediums 1022 (representing a form of a computer useable or readable medium), such as LANs, WANs, the Internet, etc. Network interface 1020 may interface with remote sites or networks via wired or wireless connections.

Control logic 1028 may be transmitted to and from computer 1000 via the communication medium 1022.

Any apparatus or manufacture comprising a computer useable or readable medium having control logic (software) stored therein is referred to herein as a computer program product or program storage device. This includes, but is not limited to, computer 1000, main memory 1008, secondary storage devices 1010, and removable storage unit 1016. Such computer program products, having control logic stored therein that, when executed by one or more data processing devices, cause such data processing devices to operate as described herein, represent embodiments of the invention.

Any apparatus or manufacture comprising a computer useable or readable medium having control logic (software) stored therein is referred to herein as a computer program product or program storage device. This includes, but is not limited to, a computer, computer main memory, secondary storage devices, and removable storage units. Such computer program products, having control logic stored therein that, when executed by one or more data processing devices, cause such data processing devices to operate as described herein, represent embodiments of the inventive techniques described herein.

IV. Conclusion

While various embodiments have been described above, it should be understood that they have been presented by way of example only, and not limitation. It will be apparent to persons skilled in the relevant art(s) that various changes in form and detail can be made therein without departing from the spirit and scope of the embodiments. Thus, the breadth and scope of the embodiments should not be limited by any of the above-described exemplary embodiments, but should be defined only in accordance with the following claims and their equivalents.

What is claimed is:

1. A measuring apparatus for determining a calf circumference of a patient for diagnosing peripheral arterial disease, comprising:
   a strip of material comprising opposing first and second surfaces, wherein at least one of the first surface or the second surface comprise:
      a first segment corresponding to a first range of calf circumference that represents a low likelihood that the patient has peripheral arterial disease,
      a second segment corresponding to a second range of calf circumference that represents a medium likelihood that the patient has peripheral arterial disease, and
      a third segment corresponding to a third range of calf circumference that represents a high likelihood that the patient has peripheral arterial disease,
   wherein the first segment, the second segment, and the third segment are arranged in series.

2. The measuring apparatus of claim 1, wherein the first segment, the second segment, and the third segment are each marked with a graphical feature corresponding to their respective likelihood that the patient has peripheral arterial disease.

3. The measuring apparatus of claim 1, wherein the first segment, the second segment, and the third segment are each marked with a textual feature corresponding to their respective likelihood that the patient has peripheral arterial disease.

4. The measuring apparatus of claim 1, wherein a respective length of each of the first segment, the second segment, and the third segment is based on statistical analysis of data associated with a plurality of patients.

5. The measuring apparatus of claim 1, wherein the first surface further comprises a first indicator that represents a mean plus standard deviation of the patients that have peripheral arterial disease.

6. The measuring apparatus of claim 1, wherein the first segment and the second segment are separated by a first segment marker, and the second segment and the third segment are separated by a third segment marker.

7. The measuring apparatus of claim 1, wherein the at least one of the first surface or the second surface further comprise:
   a fourth segment in series with the first segment, adjacent to the first segment, and configured to be held by a user that wraps measuring apparatus around the calf of the patient.

8. The measuring apparatus of claim 1, wherein the first range comprises values greater than 43 centimeters and the second range comprises values less than 43 centimeters.

\* \* \* \* \*